United States Patent
Kay et al.

(10) Patent No.: US 7,205,327 B2
(45) Date of Patent: Apr. 17, 2007

(54) IMIDAZOLE AND BENZIMIDAZOLE CASPASE INHIBITORS AND USES THEREOF

(75) Inventors: David Kay, Wiltshire (GB); Julian M. C. Golec, Swindon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 367 days.

(21) Appl. No.: 10/012,722

(22) Filed: Nov. 19, 2001

(65) Prior Publication Data

US 2002/0169177 A1 Nov. 14, 2002

Related U.S. Application Data

(60) Provisional application No. 60/252,252, filed on Nov. 21, 2000.

(51) Int. Cl.
- *C07D 233/54* (2006.01)
- *A61K 31/415* (2006.01)
- *A61P 9/10* (2006.01)

(52) U.S. Cl. ..................... 514/400; 548/338.1

(58) Field of Classification Search ............ 514/263.1, 514/303, 394, 396; 544/277; 546/118; 548/308.4, 548/338.1
See application file for complete search history.

(56) References Cited

U.S. PATENT DOCUMENTS

| | | | |
|---|---|---|---|
| 5,714,484 A | 2/1998 | Zimmerman et al. | .... 514/231.5 |
| 5,716,929 A | 2/1998 | Bemis et al. | ................. 514/18 |

2004/0192743 A1 * 9/2004 Mjalli et al. ................. 514/365

FOREIGN PATENT DOCUMENTS

| | | | |
|---|---|---|---|
| WO | 95/35308 | * | 12/1995 |
| WO | WO 98/11129 | | 3/1998 |

* cited by examiner

*Primary Examiner*—Bruck Kifle
(74) *Attorney, Agent, or Firm*—Lisa A. Dixon; Vertex Pharmaceuticals Incorporated

(57) ABSTRACT

This invention provides caspase inhibitors having the formula:

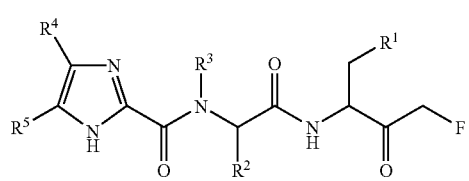

wherein $R^1$ is $CO_2H$, $CH_2CO_2H$, or esters, amides or isosteres thereof; $R^2$ and $R^3$ are each independently selected from hydrogen or an optionally substituted $C_1$–$C_6$ aliphatic group; and $R^4$ and $R^5$ are each independently selected from hydrogen, an optionally substituted $C_1$–$C_6$ aliphatic group, or $R^4$ and $R^5$ taken together with the ring to which they are attached form an optionally substituted bicyclic ring. The caspase inhibitors are useful for treating a number of diseases such as cancer, acute inflammatory and autoimmune disorders, ischemic diseases and certain neurodegenerative disorders.

11 Claims, No Drawings

IMIDAZOLE AND BENZIMIDAZOLE CASPASE INHIBITORS AND USES THEREOF

CROSS REFERENCE TO RELATED APPLICATIONS

This application claims priority to U.S. Provisional Patent Application No. 60/252,252 filed Nov. 21, 2000.

FIELD OF THE INVENTION

This invention is in the field of medicinal chemistry and relates to novel compounds, and pharmaceutical compositions thereof, that inhibit caspases that mediate cell apoptosis and inflammation. The invention also relates to methods of using the compounds and pharmaceutical compositions of this invention to treat diseases where caspase activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally Science, 1998, 281, 1283–1312; Ellis et al., *Ann. Rev. Cell. Biol.*, 1991, 7, 663).

Caspases are a family of cysteine protease enzymes that are key mediators in the signaling pathways for apoptosis and cell disassembly (Thornberry, *Chem. Biol.*, 1998, 5, R97–R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1β ("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, and 5, has been shown to prefer hydrophobic aromatic amino acids at position 4 on the N-terminal side of the cleavage site. Another group which includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 4.

The caspases have also been grouped according to their putative function. The first subfamily consists of caspases-1 (ICE), 4, and 5. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon gamma inducing factor (IGIF or IL-18) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector capsases 3, 6 and 7, are involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

Knowledge of the four amino acid sequence primarily recognized by the caspases has been used to design caspase inhibitors. Reversible tetrapeptide inhibitors have been prepared having the structure $CH_3CO$-[P4]-[P3]-[P2]-CH(R)$CH_2CO_2H$ where P2 to P4 represent an optimal amino acid recognition sequence and R is an aldehyde, nitrile or ketone capable of binding to the caspase cysteine sulfhydryl. Rano and Thornberry, *Chem. Biol.* 4, 149–155 (1997); Mjalli, et al., *Bioorg. Med. Chem. Lett.* 3, 2689–2692 (1993); Nicholson et al., *Nature* 376, 37–43 (1995). Irreversible inhibitors based on the analogous tetrapeptide recognition sequence have been prepared where R is an acyloxymethylketone —$COCH_2OCOR'$. R' is exemplified by an optionally substituted phenyl such as 2,6-dichlorobenzoyloxy and where R is $COCH_2X$ where X is a leaving group such as F or Cl. Thornberry et al., *Biochemistry* 33, 3934 (1994); Dolle et al., *J Med. Chem.* 37, 563–564 (1994).

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock. Yaoita et al., *Circulation*, 97, 276 (1998); Endres et al., *J Cerebral Blood Flow and Metabolism*, 18, 238, (1998); Cheng et al., J. Clin. Invest., 101, 1992 (1998); Yakovlev et al., *J Neuroscience*, 17, 7415 (1997); Rodriquez et al., *J. Exp. Med.*, 184, 2067 (1996); Grobmyer et al., *Mol. Med.*, 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism. Plattner and Norbeck, in *Drug Discovery Technologies*, Clark and Moos, Eds. (Ellis Horwood, Chichester, England, 1990).

Recognizing the need to improve the pharmacological properties of the peptidic caspase inhibitors, peptidomimetic and non-natural amino acid peptide inhibitors have been reported.

WO 95/35308 discloses inhibitors of interleukin-1β converting enzyme including, inter alia, compounds of the formulae:

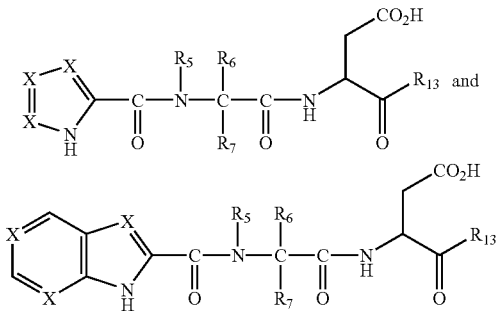

wherein X is independently selected from =N— or =CH—; $R_5$ includes hydrogen; $R_7$ is hydrogen and $R_6$ includes an α-amino acid side chain; and $R_{13}$ includes hydrogen, an aromatic or heteroaromatic ring, a $C_1$–$C_6$ straight or branched alkyl group singly or multiply optionally substituted by F. WO 95/35308 reports those compounds to be active against ICE and does not report activity against other caspases.

WO 98/10778 discloses inhibition of apoptosis using interleukin-1β-converting enzyme (ICE)/CED-3 family inhibitors of formula:

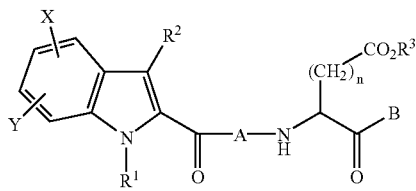

wherein n is 1 or 2; $R^1$, $R^2$, and $R^3$ are various groups; A is a natural or unnatural amino acid; B includes, inter alia, a halomethyl group; and X and Y are various substituents.

WO 00/061542 discloses dipeptide apoptosis inhibitors having the formula:

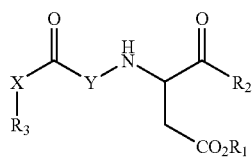

where $R_1$ is an optionally substituted alkyl or hydrogen group; $R_2$ is hydrogen or optionally substituted alkyl; Y is a residue of a natural or non-natural amino acid and $R_3$ is an alkyl, saturated carbocyclic, partially saturated carbocyclic, aryl, saturated heterocyclic, partially saturated heterocyclic or heteroaryl group, wherein said group is optionally substituted; X is O, S, $NR_4$, or $(CR_4R_5)_n$ where $R_4$ and $R_5$ are, at each occurrence, independently selected from the group consisting of hydrogen, alkyl and cycloalkyl, and n is 0, 1, 2, or 3; or X is $NR_4$, and $R_3$ and $R_4$ are taken together with the nitrogen atom to which they are attached to form a saturated heterocyclic, partially saturated heterocyclic or heteroaryl group, wherein said group is optionally substituted or X is $CR_4R_5$, and $R_3$ and $R_4$ are taken together with the carbon atom to which they are attached to form a saturated carbocyclic, partially saturated carbocyclic, aryl, saturated heterocyclic, partially saturated heterocyclic or oxygen-containing heteroaryl group, wherein said group is optionally substituted; and provided that when X is O, then $R_3$ is not unsubstituted benzyl or t-butyl; and when X is $CH_2$, then $R_3$ is not H.

While a number of caspase inhibitors have been reported, it is not clear whether they possess the appropriate pharmacological properties to be therapeutically useful. Therefore, there is a continued need for small molecule caspase inhibitors that are potent, stable, and penetrate membranes to provide effective inhibition of apoptosis in vivo. Such compounds would be extremely useful in treating the aforementioned diseases where caspase enzymes play a role.

SUMMARY OF THE INVENTION

It has now been found that compounds of this invention and pharmaceutical compositions thereof are particularly effective as inhibitors of caspases and cellular apoptosis. These compounds have the general formula I:

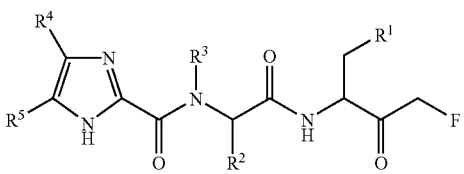

wherein:
$R^1$ is $CO_2H$, $CH_2CO_2H$, or esters, amides or isosteres thereof;
$R^2$ is hydrogen or an optionally substituted $C_1$–$C_6$ aliphatic group;
$R^3$ is hydrogen or an optionally substituted $C_1$–$C_6$ aliphatic group; and
$R^4$ and $R^5$ are each independently selected from hydrogen, an optionally substituted $C_1$–$C_6$ aliphatic group, or $R^4$ and $R^5$ taken together with the ring to which they are attached form an optionally substituted bicyclic ring, said bicyclic ring selected from the following:

(a)
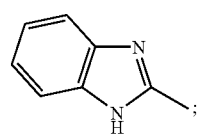

(b)
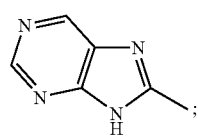

(c)

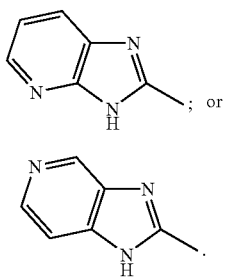
; or (d)

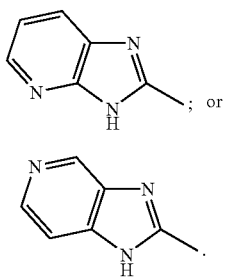
.

The compounds of this invention have potent inhibition properties across a range of caspase targets with good efficacy in cellular models of apoptosis. In addition, these compounds are expected to have improved cell penetration and pharmacokinetic properties and, as a consequence of their potency, have improved efficacy against diseases where caspases are implicated.

DETAILED DESCRIPTION OF THE INVENTION

This invention provides novel compounds, and pharmaceutically acceptable derivatives thereof, that are particularly effective as caspase inhibitors. The invention also provides methods for using the compounds to treat caspase-mediated disease states in mammals. The compounds have the general formula I:

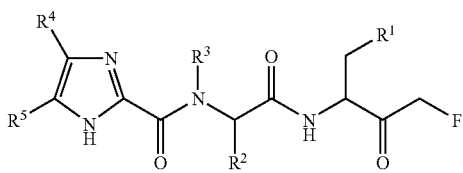

wherein:

$R^1$ is $CO_2H$, $CH_2CO_2H$, or esters, amides or isosteres thereof;

$R^2$ is hydrogen or an optionally substituted $C_1$–$C_6$ aliphatic group;

$R^3$ is hydrogen or an optionally substituted $C_1$–$C_6$ aliphatic group; and $R^4$ and $R^5$ are each independently selected from hydrogen, an optionally substituted $C_1$–$C_6$ aliphatic group, or $R^4$ and $R^5$ taken together with the ring to which they are attached form an optionally substituted bicyclic ring, said bicyclic ring selected from the following:

(a)

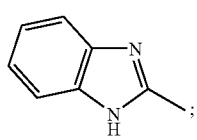
;

(b)

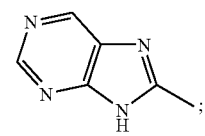
;

(c)

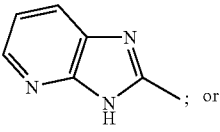
; or (d)

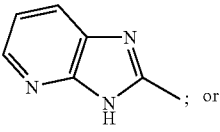
.

The term "aliphatic" as used herein means straight-chain, branched or cyclic $C_1$–$C_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl) alkyl or (cycloalkyl)alkenyl. The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms. The term "cycloalkyl" used alone or as part of a larger moiety shall include cyclic $C_3$–$C_{12}$ hydrocarbons which are completely saturated or which contain one or more units of unsaturation, but which are not aromatic.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The terms "carbocycle", "carbocyclyl", "carbocyclo", or "carbocyclic" as used herein means an aliphatic ring system having three to fourteen members.

The terms "carbocycle", "carbocyclyl", "carbocyclo", or "carbocyclic" whether saturated or partially unsaturated, also refers to rings that are optionally substituted. The terms "carbocycle", "carbocyclyl", "carbocyclo", or "carbocyclic" also include aliphatic rings that are fused to one or more aromatic or nonaromatic rings, such as in a decahydronaphthyl, tetrahydronaphthyl, or indanyl where the radical or point of attachment is on the aliphatic ring.

The term "aryl" used alone or as part of a larger moiety as in "aralkyl", "aralkoxy", or "aryloxyalkyl", refers to aromatic ring groups having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having five to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, tetrahydroquinolinyl, or tetrahydroisoquinolinyl where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, N-imidazolyl, 2-imidazolyl, 4-imidazolyl, 5-imidazolyl, 3-furazanyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on the unsaturated carbon atom of an aryl, heteroaryl, aralkyl, or heteroaralkyl group include a halogen, —R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C((=NH)—N(R°)$_2$, —(CH$_2$)$_y$NHC(O)R°, —(CH$_2$)$_y$NHC(O)CH(V—R°)(R°); wherein R° is hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph); y is 0-6; and V is a linker group. Examples of substituents on the aliphatic group or the phenyl ring of R° include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the nitrogen of a non-aromatic heterocyclic ring include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, and —NR$^+$SO$_2$R$^+$; wherein R$^+$ is hydrogen, an aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

When the R$^1$ group is in the form of an ester or amide, the present compounds undergo metabolic cleavage in a mammal to the corresponding carboxylic acids, which are the active caspase inhibitors. Because they undergo metabolic cleavage, the precise nature of the ester or amide group is not critical to the working of this invention. The structure of the R$^1$ group may range from the relatively simple diethyl amide to a steroidal ester. Examples of esters of $R^1$ carboxylic acids include, but are not limited to, $C_{1-12}$ aliphatic, such as $C_{1-6}$ alkyl or $C_{3-10}$ cycloalkyl, aryl, such as phenyl, aralkyl, such as benzyl or phenethyl, heterocyclyl, heterocyclylalkyl, heteroaryl, and heteroaralkyl. Examples of suitable $R^1$ heterocyclyl rings include, but are not limited to, 5–6 membered heterocyclic rings having one or two heteroatoms such as piperidinyl, piperazinyl, or morpholinyl. Examples of suitable $R^1$ heteroaryl rings include, but are not limited to, 5–6 membered heteroaryl rings having one or two heteroatoms such as pyridyl, pyrimidinyl, furanyl and thienyl.

Amides of $R^1$ carboxylic acids may be primary, secondary or tertiary. Suitable substituents on the amide nitrogen include, but are not limited to, one or two groups independently selected from the aliphatic, aryl, aralkyl, heterocyclyl, heterocyclylalkyl, heteroaryl and heteroaralkyl groups described above for the $R^1$ ester alcohol. Likewise, other prodrugs are included within the scope of this invention. See Bradley D. Anderson, "Prodrugs for Improved CNS Delivery" in Advanced Drug Delivery Reviews (1996), 19, 171–202.

Isosteres or bioisosteres of $R^1$ carboxylic acids, esters and amides result from the exchange of an atom or group of atoms to create a new compound with similar biological properties to the parent carboxylic acid or ester. The bioisosteric replacement may be physicochemically or topologically based. An example of an isosteric replacement for a carboxylic acid is $CONHSO_2(alkyl)$ such as $CONHSO_2Me$.

Compounds of this invention where $R^1$ is $CO_2H$ or $CH_2CO_2H$, γ-ketoacids or δ-ketoacids respectively may exist in solution as either the open form (a) or the cyclized hemiketal form (b) (y=1 for γ-ketoacids, y=2 for δ-ketoacids). The representation herein of either isomeric form is meant to include the other.

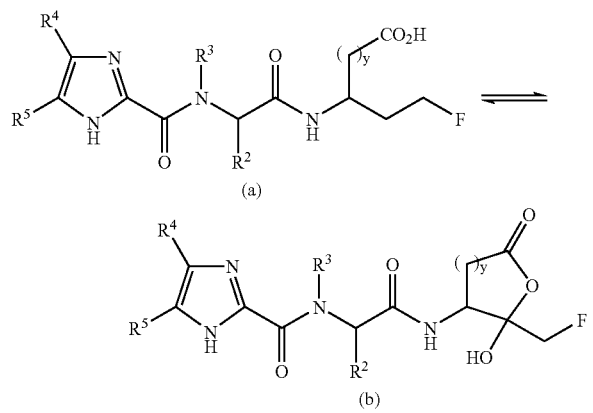

Likewise it will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

A number of dipeptidic ICE/caspase inhibitors that were generically described in WO 95/35308 have now been tested for activity against caspases in the enzymatic and cell-based assays described below. Among the compounds tested, the new compounds of formula I were found to have unexpectedly good activity against a number of caspase enzymes.

When $R^4$ and $R^5$ are taken together to form a ring fused to the imidazole, the following embodiments of this invention are provided:

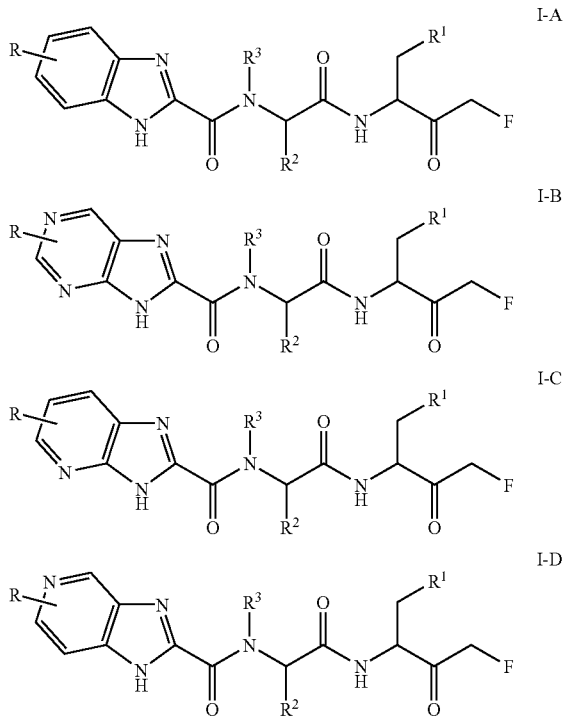

where $R^1$, $R^2$ and $R^3$ are as described above and R represents one or more optional substituents. Examples of R groups, when attached to a position nonadjacent to a ring nitrogen, include $C_{1-6}$ alkyl, $C_{1-6}$ alkoxy, halo, alkylamino, dialkylamino, alkylaminocarbonyl, dialkylaminocarbonyl, and alkylcarbonyl. Examples of R groups, when attached to a position adjacent to a ring nitrogen, include $C_{1-6}$ alkyl, alkylamino, and dialkylamino.

Preferred compounds of this invention are compounds of formula I that have one or more of the following features and more preferably all of the following features:

(a) $R^1$ is $CO_2H$ or esters, amides or isosteres thereof;

(b) $R^2$ is a $C_1$-$C_6$ straight chain or branched alkyl group;

(c) $R^3$ is hydrogen; and (d) $R^4$ and $R^5$ are each hydrogen, or $R^4$ and $R^5$ together with the ring to which they are attached form a benzimidazole ring.

When $R^2$ is substituted, preferred substituents include hydroxy, thio, amino or halogen.

Specific representative examples of compounds of formula I are shown in Table 1.

| No. | A Ring | $R^1$ | $R^2$ | $R^3$ |
|---|---|---|---|---|
| 1 | Imidazol-2-yl | $CO_2H$ | $CH_3-$ | H |
| 2 | Benzimidazol-2-yl | $CO_2H$ | $CH_3-$ | H |
| 3 | Imidazol-2-yl | $CO_2H$ | $CH_3CH_2-$ | H |
| 4 | Imidazol-2-yl | $CO_2H$ | $(CH_3)_2CH-$ | H |
| 5 | Benzimidazol-2-yl | $CO_2H$ | $(CH_3)_2CH-$ | H |
| 6 | 9H-Purin-8-yl | $CO_2H$ | $(CH_3)_2CH-$ | H |
| 7 | 3H-Imidazo[4,5-b]pyridin-2-yl | $CO_2H$ | $(CH_3)_2CH-$ | H |

The compounds of this invention may be prepared in general by methods known to those skilled in the art for analogous compounds, as illustrated by the general Scheme I below and by the preparative examples that follow.

Scheme I shows a general route to prepare the present compounds. The following abbreviations are used: EDC is 1-(3-dimethylaminopropyl)-3-ethylcarbodiimide; HOBT is 1-hydroxybenzotriazole; TFA is trifluoroacetic acid; DCM is dichloromethane; and DMAP is 4-dimethylaminopyridine. Reaction of the known imidazole-2-carboxylic acid or the known benzimidazole-2-carboxylic acid (represented by generic structure 1) with amino ester derivative 2 provides amide 3. If the ester 3 is a tert-butyl ester, TFA in DCM is used to provide the acid 4. For other R groups, standard hydrolysis may be used. The acid 4 is then coupled with the amino alcohol 5 to provide 6. Depending on the nature of R an amino ketone may be used, in place of the amino alcohol 5, which avoids the subsequent oxidation step. In the case of fluoromethyl ketones where $CO_2R$ is $CO_2tBu$, the amino alcohol 5 may be obtained according to the method of Revesz et al., *Tetrahedron Lett.*, 1994, 35, 9693. Finally the hydroxyl in compound 6 is oxidized and the compound then treated appropriately according to the nature of $R^1$. For example, if the product I requires $R^1$ to be a carboxylic acid, then $R^1$ in 7 is preferably an ester and the final step in the scheme is hydrolysis.

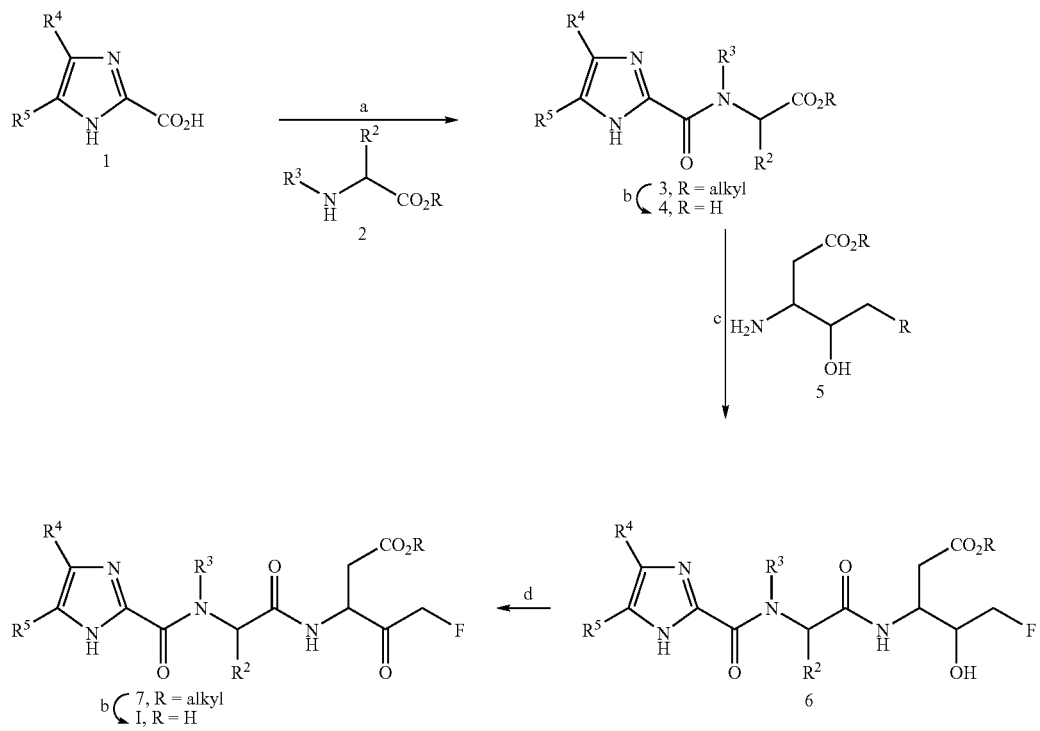

Reagents: (a) EDC, diisopropylethylamine, HOBt, 2; (b) hydrolysis or TFA/DCM; (c) DMAP, EDC, diisopropylethylamine, HOBt, 4; (d) Dess-Martin periodinane

EXPERIMENTAL

Example 1

[3S/R,(2S)]-5-Fluoro-3-{2-[(1H-imidazole-2-carbonyl)-amino]-propionylamino}-4-oxo-pentanoic acid, trifluoroacetate salt (Compound 1)

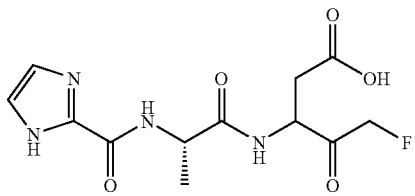

Method A (2S)-2-[(1H-Imidazole-2-carbonyl)-amino]-propionic acid tert-butyl ester

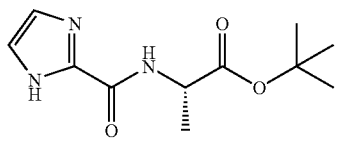

To a solution of 1H-imidazole-2-carboxylic acid (0.17 g) in N,N-dimethylformamide (DMF) (3 mL) was added alanine tert-butyl ester hydrochloride(0.22 g), diisopropylethyl amine (0.27 mL) and HOBT (0.41 g) before cooling to 0° C. and reaction mixture treated with EDC.HCl (0.32 g). The cooling bath was removed and the reaction mixture stirred at ambient temperature for 18 hrs before being diluted with ethyl acetate and washed with water and brine, dried (MgSO$_4$) and concentrated at reduced pressure. The residue was purified by silica gel chromatography (30% ethyl acetate in hexanes) to afford the sub-title compound as a colourless oil (0.263 g, 73%): $^1$H NMR 400 MHz CDCl3 1.50 (9H, s), 1.51 (3H, d, J 7.2), 3.70 (1H, m), 7.28 (2H, s), 7.78 (1H, d, J 7.6), 11.49 (1H, br s).

Method B

[3S/R, 4S/R, (2S)]-5-Fluoro-4-hydroxy-3-{2-[(1H-imidazole-2-carbonyl)-amino]-propionylamino}-pentanoic acid tert-butyl ester

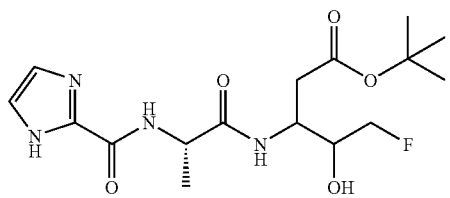

A solution of (2S)-2-[(1H-imidazole-2-carbonyl)-amino]-propionic acid tert-butyl ester (0.257 g) in dichloromethane (2 mL) was cooled to 0° C. before dropwise addition of trifluoroacetic acid and reaction mixture warmed to room temperature and stirred for 2 hr before evaporation under reduced pressure. The residue was co-evaporated with dichloromethane (twice) and toluene (twice) to leave the required (2S)-2-[(1H-imidazole-2-carbonyl)-amino]-propionic acid that was used without further purification (0.40 g).

A solution of (2S)-2-[(1H-imidazole-2-carbonyl)-amino]-propionic acid and 3-amino-5-fluoro-4-hydroxy-pentanoic acid tert-butyl ester (0.254 g) in THF (7 mL) was cooled to 0° C. before addition of DMAP (0.151 g), diisopropylethyl amine (0.56 mL), HOBT (0.16 g) and EDC.HCl (0.23 g). The reaction mixture stirred at ambient temperature for 18 hrs before being concentrated at reduced pressure. The residue was purified by silica gel chromatography (5% methanol in dichloromethane) to afford the sub-title compound as a colourless solid (0.386 g, 97%): $^1$H NMR 400 MHz CDCl3/CD3OD 1.40 (12H, m), 3.92 (1H, m), 4.20–4.55 (4H, m), 7.11 (2H, d, J 15) $^{19}$F NMR CDCl$_3$–229.74 (m), –229.84 (m), –230.54 (m), –230.87 (m).

Method C

[3S/R,(2S)]-5-Fluoro-3-{2-[(1H-imidazole-2-carbonyl)-amino]-propionylamino}-4-oxo-pentanoic acid tert-butyl ester

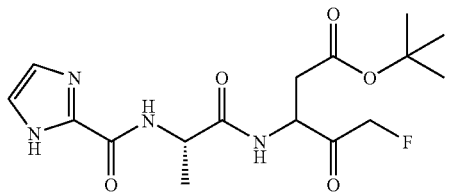

A solution of [3S/R,(2S)]-5-fluoro-4-hydroxy-3-{2-[(1H-imidazole-2-carbonyl)-amino]-propionylamino}-pentanoic acid tert-butyl ester (0.381 g) in dichloromethane was cooled to 0° C. before addition of 1,1,1 triacetoxy-1,1-dihydro-1,2-benziodoxol-3(1H)-one (0.476 g). The mixture was stirred at room temperature for 2 h before addition of an additional portion of 1,1,1 triacetoxy-1,1-dihydro-1,2-benziodoxol-3(1H)-one (0.05 g) and reaction mixture stirred for 90 min before being concentrated at reduced pressure. The residue was dissolved in ethyl acetate and washed with a 1:1 mixture of aqueous NaHSO$_4$ and aqueous Na$_2$S$_2$O$_3$. The organic layer was collected, dried (MgSO$_4$) and concentrated. The residue was purified by flash chromatography (5% methanol in dichloromethane) to give the sub-title compound as a colourless foam (319 mg, 84%): $^1$H NMR 400 MHz CDCl$_3$ 1.37+1.43 (9H, 2xs), 1.54 (3H, m), 2.85 (1H, m), 3.03 (1H, m), 4.85–5.30 (4H, m), 7.18 (2H, d, J 16), 7.90 (1H, m), 7.98 (1H, m), 11.37+11.45 (1H, 2xs); $^{19}$F NMR 376 MHz CDCl$_3$ –231.85 (t, J 48), –232.12 (t, J 48).

Method D

Compound 1

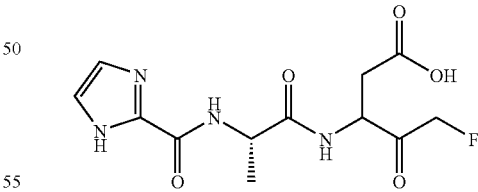

A solution of [3S/R,(2S)]-5-Fluoro-3-{2-[(1H-imidazole-2-carbonyl)-amino]-propionylamino}-4-oxo-pentanoic acid tert-butyl ester (0.31 g) in dichloromethane (2 mL) was cooled to 0° C. before dropwise addition of trifluoroacetic acid and reaction mixture warmed to room temperature and stirred for 2 hr before evaporation under reduced pressure. The residue was co-evaporated with dichloromethane (twice) and triturated under ether to give the title compound as a colourless solid (0.35 g): IR 1785.7,1730.1,1653.7, 1538.1, 1458.2, 1384.2, 1268.7, 1188.4, 1150.9, 1053.3, 992.13, 931.8, 867.9, 847.0, 768.5 cm$^{-1}$; $^1$H NMR 400 MHz DMSO D$_6$ 1.37 (3H, d), 2.40–2.85(2H,m,asp CH2); 4.34–4.75(2.5H,m,2×CH+0.5CH2F); 5.13–5.41 (1.5H,m, CH2F); 7.50(2H,s,imidazole CHs); 8.58–8,79(2H,m,NHs); $^{13}$C NMR 100 MHz DMSO D$_6$ 18.13, 18.85(ala CH$_3$); 33.13, 34.75(asp CH$_2$); 48.68,52.41(CHs); 83.46, 85.21 (CH2F); 123.67(CH imidazole); 139.57,158.86,172.35(m) (C=Os); 202.70(5 peaks ketone); $^{19}$F NMR 376 MHz DMSO D$_6$ decoupled −75.19(3F,s,CF3COOH); −(226.89, 226.96,230.80,231.59, 232.95, 233.06 (1F,6×s, COCH$_2$F ring opened and ring closed).

Example 2

[3S/R, (2S)]-3-{2-[(1H-Benzoimidazole-2-carbonyl)-amino]-propionylamino}-5-fluoro-4-oxo-pentanoic acid, trifluoroacetate salt (Compound 2)

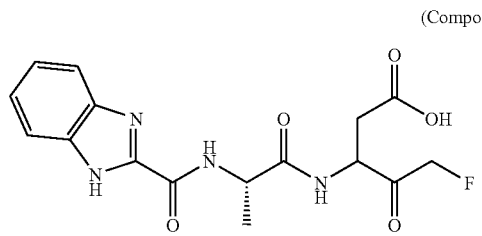

(Compound 2)

This was prepared from 1H-benzoimidazole-2-carboxylic acid using procedures similar to those described in Methods A-D above (142 mg, 90% for final step): (compound isolated as the TFA salt) Off-white solid; IR (solid, cm$^{-1}$) 3277.9, 1654.6, 1526.6, 1188.6, 1142.5, 1050.4, 927.5, 748.2, 712.4; $^1$H NMR (DMSO-D$^6$) 1.42 (3H, d), 2.51–2.95 (2H, m), 4.21–4.75(2H, m), 4.76–5.60 (3H, brm), 7.41 (2H, m), 7.65 (2H, m), 8.21–9.05 (2H, m); $^{13}$C NMR (DMSO-D$^6$) 18.0, 18.7, 18.8 (Ala CH3), 37.2, 34.6, 34.7 (Asp CH2), 47.6, 48.8, 48.85, 49.1 (Asp CH), 52.0, 52.5 (Ala CH), 83.5, 85.2, 85.3, 103.8, 106.0 (CH2F), 116.6, 123.9 (Aryl CH), 145.3, 145.4, (Aryl C), 158.4, 158.7, 158.8, 172.1, 172.2, 172.4, 172.5, 172.6, 172.7, 173.2 (NC=O), 202.6, 202.7, 202.8, 202.9 (C=O); Found M$^+$ 364.1177. C$_{16}$H$_{17}$FN$_4$O$_5$ requires M$^+$ 364.1183 (1.8 ppm)

Example 3

[3S/R,(2S)]-5-Fluoro-3-{2-[(1H-imidazole-2-carbonyl)-amino]-butyrylamino}-4-oxo-pentanoic acid, trifluoroacetate salt (Compound 3)

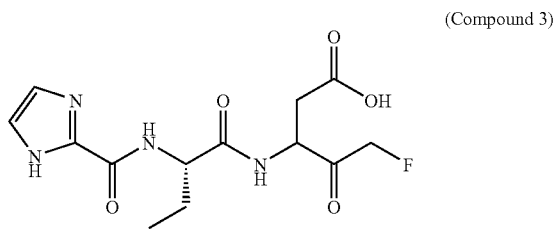

(Compound 3)

This was prepared from 1H-benzoimidazole-2-carboxylic acid using procedures similar to those described in Methods A-D above (147 mg, 64% for final step): IR 3280.0, 1659.5, 157.9, 1192.5, 1141.6, 784.7, 721.1 cm$^{-1}$; $^1$H NMR 400 MHz DMSO D$_6$ 0.95 (3H, m), 1.78 (2H, m), 2.58–2.98 (2H, m), 4.30–4.78 (2.5H, m), 5.10–5.42 (1.5H, m), 7.41 (2H, s), 8.44+8.75 (2H, 2×m); $^{13}$C NMR 100 MHz DMSO D$_6$ 10.19, 10.29, 15.52 (CH3), 25.42, 25.49, 26.03, 33.06, 33.13, 34.65, 34.80 (CH2), 47.45, 47.53, 52.0, 53.96, 54.13 (CH) 65.27 (CH2), 84.36 (d, J 177, CH2F), 103.81, 104.00 (C), 123.89 (CH), 139.74 (C=O), 156.90, 158.39, 158.74, 171.51, 171.80, 171.83, 172.02, 173.11 (C=O), 202.51, 202.66, 202.76, 202.90 (CH2FC=O); $^{19}$F NMR 376 MHz DMSO D$_6$ −226.82 (t, J 45), −226.84 (t, J 45), −230.67 (t, J 45), −231.43 (t, J 45), −232.79 (t, J 45), −232.82 (t, J 45).

Example 4

[3S/R,(2S)]-5-Fluoro-3-{2-[(1H-imidazole-2-carbonyl)-amino]-3-methylbutyrylamino}-4-oxo-pentanoic acid

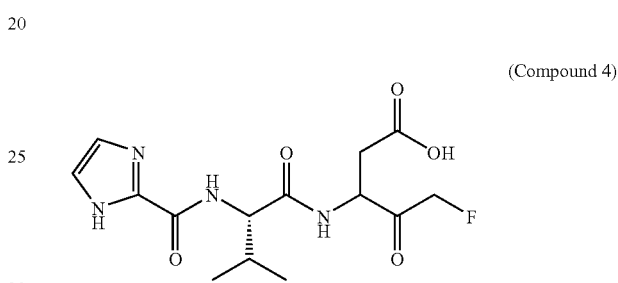

(Compound 4)

This was prepared from 1H-benzoimidazole-2-carboxylic acid using procedures similar to those described in Methods A-D above (80 g, 85% for final step): white powder, IR (solid, cm$^{-1}$) 1736, 1649, 1557, 1511, 1455, 1434, 1393; 1H NMR (DMSO+TFA) 0.92–0.95 (6H, m), 2.06-2.15 (1H, m), 2.56–2.90 (2H, m), 4.33–5.36 (4H, m), 7.79 (2H, s), 8.58–8.90 (2H, m); $^{19}$FNMR (DMSO+TFA) −226.8 (t) −230.6 (t), −231.0 (t), −232.5 (t), −232.6 (t); $^{13}$C NMR (DMSO+TFA) 18.1/18.4 (CH3), 19.2/19.3 (CH3), 34.5/34.8 (CH2), 51.9/52.2 (CH), 58.5/58.8 (CH), 84.3/84.4 (2d, J 178.7/178.7, CH2F), 122.0 (CH), 137.5 (C), 153.7 (C), 170.6 (C), 171.9/172.0 (C), 202.5/202.8 (2d, J 14.6/14.6, CO).

Example 5

[3S/R, (2S)]-3-{2-[(1H-Benzoimidazole-2-carbonyl)-amino]-3-methylbutyrylamino}-5-fluoro-4-oxo-pentanoic acid

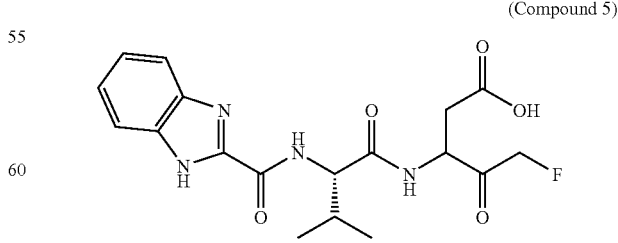

(Compound 5)

This was prepared from 1H-benzoimidazole-2-carboxylic acid using procedures similar to those described in Methods A-D above (90 mg, 87% for final step): white powder, IR (solid, cm$^{-1}$) 1737, 1665, 1527, 1373, 1194, 1137; 1H NMR (DMSO) 0.90–0.95 (6H, m), 2.15–2.18 (1H, m), 2.59–2.92 (2H, m), 4.33–4.76 and 5.12–5.38 (4H, 2m), 7.31–7.35 (2H, m), 7.66–7.68 (2H, m), 8.36–8.82 (2H, m); $^{19}$FNMR (DMSO+TFA) −226.7 (t), −226.9 (t), −232.4 (t), −232.6 (t); $^{13}$C NMR (DMSO) 18.3/18.4/18.5/18.7 (CH3), 19.4/19.5 (CH3), 31.0/31.1/31.6 (CH), 34.7/34.8 (CH2), 51.8/52.1 (CH), 57.9/58.3/58.6 (CH), 84.3/84.4 (2d, J 178.7/178.7, CH$_2$F), 124.0 (CH), 145.2/145.2 (C), 158.4/158.5/158.7/158.8 (C), 170.9/171.1/171.2 (C), 172.0/172.0 (C), 173.1 (C), 173.9 (C), 202.06/202.6 (2d, J 13.8, CO).

The compounds of this invention are designed to inhibit caspases. Therefore, the compounds of this invention can be assayed for their ability to inhibit apoptosis, the release of IL-1β or caspase activity directly. Assays for each of the activities are known in the art and are described below in detail in the Testing section.

According to another embodiment, the invention provides a composition comprising a compound of this invention or a pharmaceutically acceptable salt thereof, as described above, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a patient, preferably a human being. One aspect of this invention relates to a method of treating a caspase-related disease in a patient in need thereof, which method comprises administering to the patient a therapeutically effective amount of a compound of formula I or a pharmaceutical composition thereof. The term "patient" includes human and veterinary subjects.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful for treating caspase-related diseases. The term "caspase-related disease" refers to an IL-1 mediated disease, an apoptosis mediated disease, an inflammatory disease, an autoimmune disease, a destructive bone disorder, a proliferative disorder, an infectious disease, a degenerative disease, a disease associated with cell death, an excess dietary alcohol intake disease, a viral mediated disease, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, Shigellosis, Alzheimer's disease, Parkinson's disease, Huntington's disease, Kennedy's disease, prion disease, cerebral ischemia,epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, or Japanese encephalitis, various forms of liver disease, renal disease, polyaptic kidney disease, H. pylori-associated gastric and duodenal ulcer disease, HIV infection, tuberculosis, and meningitis.

Preferred uses of the present compositions include an IL-1 mediated disease, an apoptosis mediated disease, an inflammatory disease, an autoimmune disease, a destructive bone disorder, an infectious disease, a degenerative disease, a disease associated with cell death, an excess dietary alcohol intake disease, a viral mediated disease, uveitis, inflammatory peritonitis, osteoarthritis, pancreatitis, adult respiratory distress syndrome, glomerulonephritis, rheumatoid arthritis, diabetes, thrombocytopenia, inflammatory bowel disease, Crohn's disease, psoriasis, scarring, organ transplant rejection, osteoporosis, haemorrhagic shock, sepsis, septic shock, burns, Shigellosis, Alzheimer's disease, Parkinson's disease, Huntington's disease, Kennedy's disease, prion disease, cerebral ischemia,epilepsy, acute and chronic heart disease, coronary artery bypass graft, amyotrophic lateral sclerosis, multiple sclerosis, alopecia, ulcerative colitis, traumatic brain injury, spinal cord injury, various forms of liver disease, renal disease, H. pylori-associated gastric and duodenal ulcer disease, and meningitis.

The compounds and compositions are also useful in treating complications associated with coronary artery bypass grafts. The compounds and compositions are also particularly useful for treating cancer, either alone or in combination with another therapy such as chemotherapy or radiotherapy. The compounds and compositions also may be used as a component of immunotherapy for the treatment of various forms of cancer.

The amount of compound present in the above-described compositions should be sufficient to cause a detectable decrease in the severity of the disease or in caspase activity and/or cell apoptosis, as measured by any of the assays described in the examples.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

In order that this invention be more fully understood, the following preparative and testing examples are set forth. These examples are for the purpose of illustration only and are not to be construed as limiting the scope of the invention in any way.

Example 6

Enzyme Assays

The assays for caspase inhibition are based on the cleavage of a fluorogenic substrate by recombinant, purified human Caspases -1, -3, or -8. The assays are run in essentially the same manner as described in WO0142216.

Compounds 1–5 each possess a $k_{inact}$ value greater than 20000 $M^{-1}S^{-1}$ against each of caspase-1, caspase-3 and caspase-8.

Example 7

Inhibition of IL-1β secretion from Mixed Population of Peripheral Blood Mononuclear Cells (PBMC)

Processing of pre-IL-1β by caspase-1 may be measured in cell culture using a variety of cell sources. Human PBMC obtained from healthy donors provides a mixed population of lymphocyte and mononuclear cells that produce a spectrum of interleukins and cytokines in response to many classes of physiological stimulators. The assay conditions used for inhibition of IL-1β secretion from mixed population of peripheral blood mononuclear cells may be found in WO0142216.

The inhibitory potency of the compounds can be represented by an $IC_{50}$ value, which is the concentration of inhibitor at which 50% of the mature IL-1β is detected in the supernatant as compared to the positive controls. The compounds tested were found to provide an $IC_{50}$ value less than 1 μM for inhibition of IL-1β secretion from PBMC

Example 8

Anti-fas Induced Apoptosis Assay

Cellular apoptosis may be induced by the binding of Fas ligand (FasL) to its receptor, CD95 (Fas). Conditions for an assay to measure the effect of compounds on the inhibition of the caspase-8-mediated apoptotic pathway may be found in WO0142216.

Compounds 1–5 each were found to provide an $IC_{50}$ value less than 200 nM for the activity in the FAS induced apoptosis assay.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

What is claimed is:

1. A compound of formula I:

wherein:
$R^1$ is $CO_2H$, $CH_2CO_2H$, or esters or amides thereof;
$R^2$ is hydrogen or an optionally substituted $C_1$–$C_6$ aliphatic group;
$R^3$ is hydrogen or an optionally substituted $C_1$–$C_6$ aliphatic group; and
$R^4$ and $R^5$ are each independently hydrogen or an optionally substituted $C_1$–$C_6$ aliphatic group.

2. The compound of claim 1 where $R^2$ is an optionally substituted $C_{1-6}$ straight or branched alkyl group.

3. The compound of claim 1 having one or more features selected from the group consisting of:
a) $R^1$ $CO_2H$ or esters or amides thereof;
b) $R^2$ is a $C_1$–$C_6$ straight chain or branched alkyl group;
c) $R^3$ is hydrogen; and
d) $R^4$ and $R^5$ are each hydrogen.

4. The compound of claim 3 having the following features:
a) $R^1$ is $CO_2H$ or esters or amides thereof;
b) $R^2$ is a $C_1$–$C_6$ straight chain or branched alky group;
c) $R^3$ is hydrogen; and
d) $R^4$ and $R^5$ are each hydrogen.

5. A compound selected from the group consisting of:
[3S/R,(2S)]-5-Fluoro-3-{2-[(1H-imidazole-2-carbonyl)-amino]-propionylamino}-4-oxo-pentanoic acid;
[3S/R,(2S)]-5-Fluoro-3-{2-[(1H-imidazole-2-carbonyl)-amino]-propionylamino}-4-oxo-pentanoic acid tert-butyl ester;
[3S/R,(2S)]-5-Fluoro-3-{2-[(1H-imidazole-2-carbonyl)-amino]-butyrylamino}-4-oxo-pentanoic acid;
[3S/R,(2S)]-5-Fluoro-3-{2-[(1H-imidazole-2-carbonyl)-amino]-3-methylbutyrylamino}-4oxo-pentanoic acid;
or an addition salt thereof.

6. A pharmaceutical composition comprising a compound according to any one of claims 1–5 and a pharmaceutically acceptable carrier.

7. A method for treating a disease in a patient comprising administering to the patient a therapeutically effective amount of a compound of formula I:

wherein:
$R^1$ is $CO_2H$, $CH_2CO_2H$, or esters or amides thereof;
$R_2$ is hydrogen or an optionally substituted $C_1$–$C_6$ aliphatic group; and $R_3$ is hydrogen or an optionally substituted $C_1$–$C_6$ aliphatic group; and $R_4$ and $R_5$ are each independently hydrogen or an optionally substituted $C_1$–$C_6$ aliphatic group;

wherein the disease is selected from osteoarthritis, adult respiratory distress syndrome, rheumatoid arthritis, psoriasis, sepsis, septic shock, coronary artery bypass graft, traumatic brain injury, spinal cord injury, chronic active hepatitits, graft vs host disease, cerebral ischcmia, myocardial ischernia, myocardial infarction, atheroscelerosis, neurological damage due to stroke.

8. The method of claim 7 wherein the disease or condition is a complication associated with coronary artery bypass grafts.

9. The method according to claim 7 or claim 8 wherein the compound has one or more features selected from the group consisting of:
(a) $R^1$ is $CO_2H$ or esters or amides thereof;
(b) $R^2$ is a $C_1$–$C_6$ straight chain or branched alky group;
(c) $R^3$ is hydrogen; and
(d) $R^4$ and $R^5$ are each hydrogen.

10. The method according to claim 7 or claim 8 wherein the compound has the following features:
(a) $R^1$ is $CO_2H$ or esters or amides thereof;
(b) $R^2$ is a $C_1$–$C_6$ straight chain or branched alkyl group;
(c) $R^3$ is hydrogen; and
(d) $R^4$ and $R^5$ are each hydrogen.

11. The method according to claim 7 or claim 8 wherein the compound is selected from the group consisting of:
[3S/R,(2S)]-5-Fluoro-3-{2-[(1H-imidazole-2-carbonyl)-amino]-propionylamino}-4-oxo-pentanoic acid;
[3S/R,(2S)]-5-Fluoro-3-{2-[(1H-imidazole-2-carbonyl)-amino]-propionylamino}-4-oxo-pentanoic acid tert-butyl ester;
[3S/R,(2S)]-5-Fluoro-3-{2-[(1H-imidazole-2-carbonyl)-amino]-butyrylamino}-4-oxo-pentanoic acid;
[3S/R,(2S)]-5-Fluoro-3-{2-[(1H-imidazole-2-carbonyl)-amino]-3-methylbutyrylamino}-4-oxo-pentanoic acid;
or an addition salt thereof.

* * * * *